(12) United States Patent  
Lee et al.

(10) Patent No.: US 9,028,450 B2  
(45) Date of Patent: May 12, 2015

(54) SYRINGE CAPABLE OF MEASURING TEMPERATURE OF A PATIENT BODY AND METHOD OF MANUFACTURING THE SAME

(71) Applicant: Gwangju Institute of Science and Technology, Gwangju (KR)

(72) Inventors: Sun-Kyu Lee, Gwangju (KR); Sung-ki Nam, Gwangju (KR); Hyoung-Ihl Kim, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 0 days.

(21) Appl. No.: 13/952,144

(22) Filed: Jul. 26, 2013

(65) Prior Publication Data

US 2014/0031758 A1      Jan. 30, 2014

(30) Foreign Application Priority Data

Jul. 27, 2012   (KR) .......................... 10-2012-0082807

(51) Int. Cl.
```
A61M 5/32      (2006.01)
A61M 5/31      (2006.01)
A61B 5/01      (2006.01)
G06F 19/00     (2011.01)
```

(52) U.S. Cl.
CPC ........... *A61M 5/3286* (2013.01); *A61M 5/3129* (2013.01); *A61B 5/01* (2013.01); *A61M 2230/50* (2013.01); *A61M 2207/10* (2013.01); *A61M 5/329* (2013.01); *A61M 2005/3125* (2013.01); *G06F 19/3468* (2013.01)

(58) Field of Classification Search
CPC ............. A61M 2205/3368; A61M 2205/3372; A61M 2230/50; A61M 5/3129; A61M 5/3286; A61M 2005/3125; A61M 5/329; A61B 5/01; G06F 19/3468
USPC .......... 604/181, 187, 272, 239, 531; 374/100, 374/141, 205, 101–106, 162, 155, 179, 374/208; 116/216
See application file for complete search history.

(56) References Cited

U.S. PATENT DOCUMENTS 4,038,519 A * 7/1977 Foucras ........................ 392/472
2011/0277803 A1   11/2011 Grande et al.

FOREIGN PATENT DOCUMENTS

EP            0850015 B1     2/2004

* cited by examiner

*Primary Examiner* — Bhisma Mehta  
*Assistant Examiner* — William Frehe  
(74) *Attorney, Agent, or Firm* — Lowe Hauptman & Ham, LLP

(57) ABSTRACT

Disclosed are a syringe capable of measuring an inner temperature of a patient body and a method of manufacturing the same. In the syringe, a different metal from that of a syringe needle is deposited on an inclined surface of a tip portion of the syringe needle to form a thermocouple junction with the metal of the syringe needle, whereby the region causing pain in a patient body can be diagnosed while allowing administration of medicine thereto, thereby enabling efficient treatment and significantly reducing potential harm due to drug abuse.

17 Claims, 7 Drawing Sheets

Fig. 5
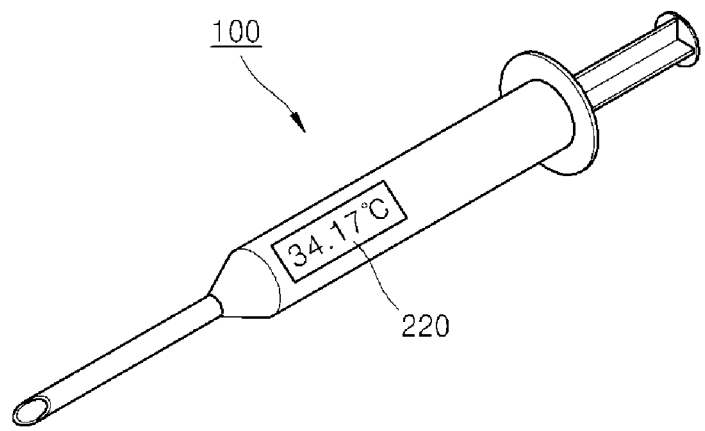
[Fig. 6]
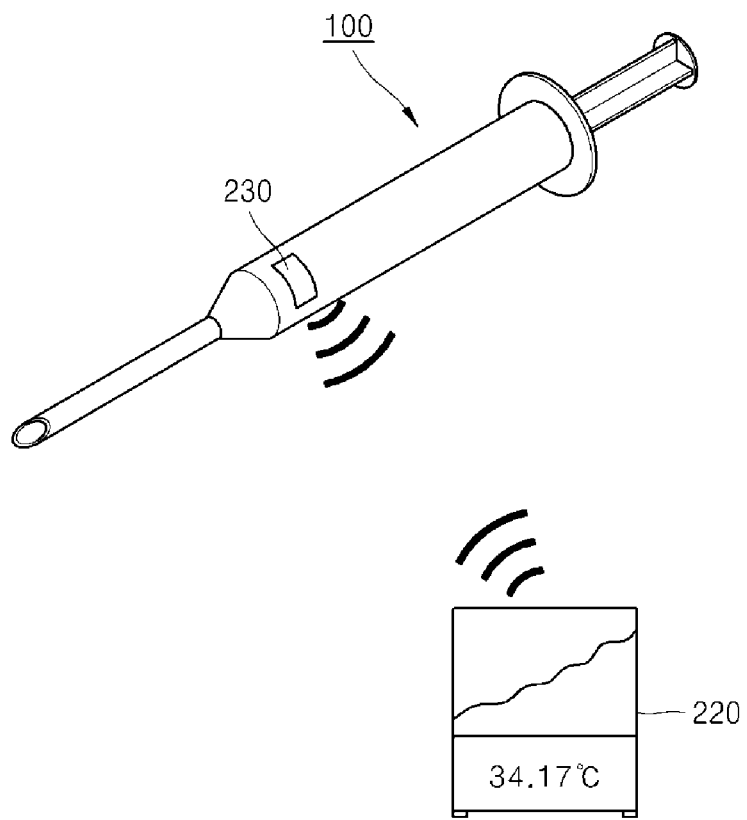

SYRINGE CAPABLE OF MEASURING TEMPERATURE OF A PATIENT BODY AND METHOD OF MANUFACTURING THE SAME

CROSS-REFERENCE TO RELATED APPLICATION

This application claims priority to Korean Patent Application No. 10-2012-0082807 filed on 27 Jul., 2012 and all the benefits accruing therefrom under 35 U.S.C. §119, the contents of which are incorporated by reference in their entirety.

BACKGROUND

1. Technical Field

The present invention relates to a syringe capable of measuring an inner temperature of a patient body and a method of manufacturing the same, and more particularly, to a syringe capable of measuring an inner temperature of a patient body, in which a different metal different from that of a syringe needle is deposited on an inclined surface of a tip portion of the syringe needle to form a thermocouple junction with the metal of the syringe needle to measure temperature of a region causing pain in a patient body, thereby enabling efficient treatment of the patient through diagnosis of the region causing pain and administration of medicine while significantly reducing potential harm due to drug abuse, and a method of manufacturing the same.

2. Description of the Related Art

A syringe is a medical instrument for administering a medicine (injection) into a human body through a hole in a hypodermic needle.

A disposable syringe is generally used to prevent secondary infection through reuse of the syringe when administering medicine to a patient.

In order to properly use a syringe, it is necessary to administer medicine into a source of pain after accurately locating the region causing pain.

A free field cylinder in the art has a temperature display function, which includes a cylinder for containing a medicine, a piston for pressing the medicine to discharge the medicine from the cylinder, a temperature display unit placed on an outer surface of the cylinder to display the temperature of the medicine in the cylinder, and a thermochromic pigment secured to the temperature display unit and reacting at a predetermined color changing temperature.

However, the free field syringe having a temperature display function is configured to measure and display only a temperature of the medicine in the syringe, and is inconvenient in that the temperature of a region causing pain in a patient body must be separately identified.

A syringe in the art includes a temperature measuring thermistor, which is inserted into a syringe needle to measure an inner temperature of a patient body after a temperature measuring needle secured by an epoxy resin is inserted into the skin.

However, although the syringe having a temperature measuring thermistor can detect the inner temperature of a patient body through the syringe needle, it is difficult to directly administer medicine into the body through the syringe.

In the related art, diagnosis using ultrasound waves, thermal images, or an electric field and administration of medicine are separately performed in treatment of musculoskeletal system pain disorder, thereby making it difficult to achieve accurate treatment of pain while increasing a danger of side effects due to drug abuse.

Therefore, there is a need for a syringe capable of conveniently measuring an inner temperature of a patient body without side effects to allow both diagnosis of a region causing pain and administration of medicine.

BRIEF SUMMARY

In order to solve such problems, the present inventors have made an effort to develop a syringe capable of measuring an inner temperature of a patient body, and found that the inner temperature of a patient body can be measured based on thermo-electromotive force from a thermocouple by depositing a different metal from that of a syringe needle on an inclined surface of a tip portion of the syringe needle to form a thermocouple junction contacting the inclined surface of the syringe needle.

It is an aspect of the present invention to provide a syringe capable of easily measuring an inner temperature of a patient body using a thermocouple junction.

In accordance with one aspect of the present invention, a syringe capable of measuring an inner temperature of a patient body is provided. The syringe includes: a first insulation layer formed by coating an insulating material on a surface of a metallic syringe needle; a dissimilar metal layer formed by depositing a different metal from that of the syringe needle on an inclined surface of a tip portion of the syringe needle to contact the inclined surface of the tip portion of the syringe needle; and a second insulation layer formed by coating an insulating material on the dissimilar metal layer.

In accordance with another aspect of the present invention, a method of manufacturing a syringe capable of measuring an inner temperature of a patient body is provided. The method includes 1) coating an insulating material on a surface of a metallic syringe needle; 2) exposing the metallic syringe needle to an outside on an inclined surface of a tip portion of the syringe needle; 3) depositing a dissimilar metal layer formed of a different metal from that of the syringe needle on the insulation material such that the dissimilar metal layer contacts the metallic syringe needle exposed to the outside; and 4) coating an insulating material on the dissimilar metal layer.

BRIEF DESCRIPTION OF THE DRAWINGS

The above and other aspects, features, and advantages of the present invention will become apparent from the detailed description of the following embodiments in conjunction with the accompanying drawings, in which:

FIG. 5 is a diagram showing a state in which a temperature display unit is attached to a body of the syringe;

FIG. 6 is a diagram showing a state in which the syringe and the temperature display unit are connected by remote connection using a wireless data transmission module;

DETAILED DESCRIPTION

Figure 1:
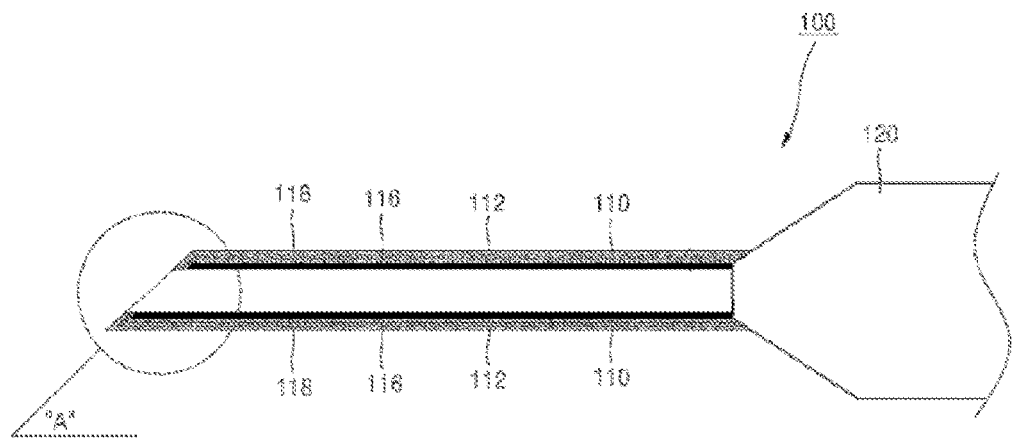
FIG. 1 is a partial section view of a syringe capable of measuring an inner temperature of a patient body in accordance with one embodiment of the present invention.

Hereinafter, embodiments of the invention will be described in detail with reference to the accompanying drawings. It should be understood that the present invention is not limited to the following embodiments and may be embodied in different ways, and that the embodiments are given to provide complete disclosure of the invention and to provide thorough understanding of the invention to those skilled in the art. The scope of the invention is limited only by the accompanying claims and equivalents thereof. Like components will be denoted by like reference numerals throughout the specification.

Syringe Capable of Measuring Inner Temperature of Human Body

Figure 2:
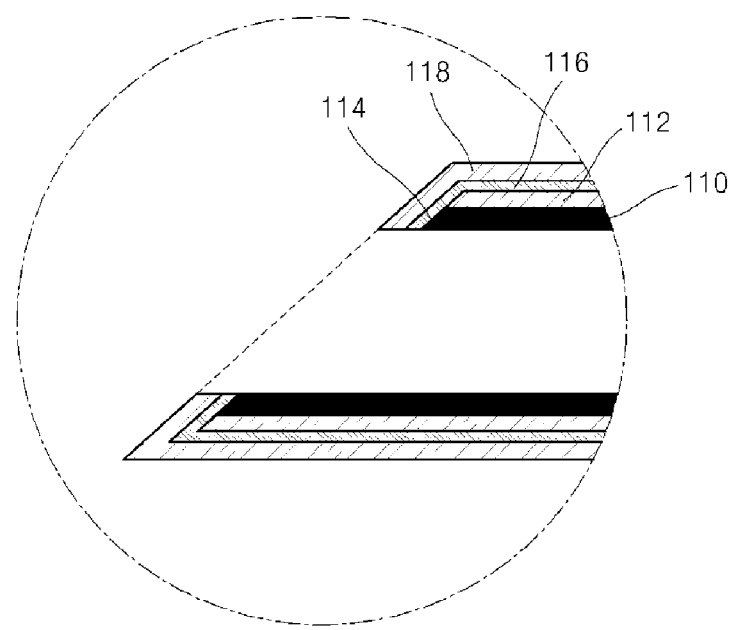
FIG. 2 is an enlarged view of part 'A' corresponding to a tip portion of a syringe needle of FIG. 1.

FIG. 1 is a partial section view of a syringe capable of measuring an inner temperature of a patient body in accordance with one embodiment of the present invention, and FIG. 2 is an enlarged view of part 'A' corresponding to a tip portion of a syringe needle of FIG. 1.

The syringe 100 according to one embodiment of the invention includes a syringe needle 110 formed of metal, and a body 120.

The metallic syringe needle 110 includes a first insulation layer 112 formed on a surface thereof by coating an insulating material thereon. Although the insulating material is deposited on the surface of the syringe needle 110 through vapor deposition, the first insulation layer is removed from an inclined surface 114 of a tip portion of the syringe needle through mechanical polishing or wet etching. As a result, the first insulation layer is not present on the inclined surface of the tip portion of the syringe needle.

In addition, the syringe needle 110 includes a dissimilar metal layer 116, which is formed by depositing a different metal from the metal of the syringe needle on the inclined surface 114 of the tip portion of the syringe needle to contact the inclined surface 114 of the tip portion of the syringe needle. A thermocouple junction is formed in an area where the inclined surface 114 of the tip portion of the syringe needle contacts the dissimilar metal layer 116. When two dissimilar metals contact each other, electric current is generated between a temperature measuring junction and a reference junction, thus generating thermo-electromotive force, which is called the Seebeck effect. A temperature at the thermocouple junction can be measured by detecting a thermo-electromotive force between the metal of the syringe needle and the dissimilar metal, which form the thermocouple junction through the Seebeck effect.

The syringe needle 110 further includes a second insulation layer 118 formed by coating an upper surface of the dissimilar metal layer 116 with an insulating material.

Any insulating material allowing vapor deposition may be used as the insulating material constituting the first insulation layer 112 and the second insulation layer 118. Preferably, parylene, polyimide, or epoxy resins may be used.

The first insulation layer 112 separates the syringe needle from the dissimilar metal layer, and the second insulation layer 118 provides an insulation coating to the dissimilar metal layer to prevent noise from outside. The thicknesses of the first insulation layer and the second insulation layer are not specifically limited, but may be adjusted to secure these functions. Preferably, each of the first insulation layer and the second insulation layer has a thickness of 0.1 μm to 100 μm.

The material for the syringe needle 110 and the metal for the dissimilar metal layer 116 are not limited so long as they are different materials capable of forming a thermocouple junction. However, the syringe needle 110 is preferably formed of iron or copper, and the dissimilar metal 116 is preferably formed of constantan, gold, or nickel. Most preferably, the syringe needle 110 is formed of iron and the dissimilar metal layer 116 is formed of constantan, such that a J type thermocouple junction is formed on the inclined surface 114 of the tip portion of the syringe needle.

It is advantageous that the dissimilar metal layer 116 has a thickness of 0.01 μm to 10 μm to act as a thermocouple based on a thermocouple phenomenon. More preferably, the dissimilar metal layer 116 has a thickness of 0.1 μm to 1.0 μm.

Figure 3:
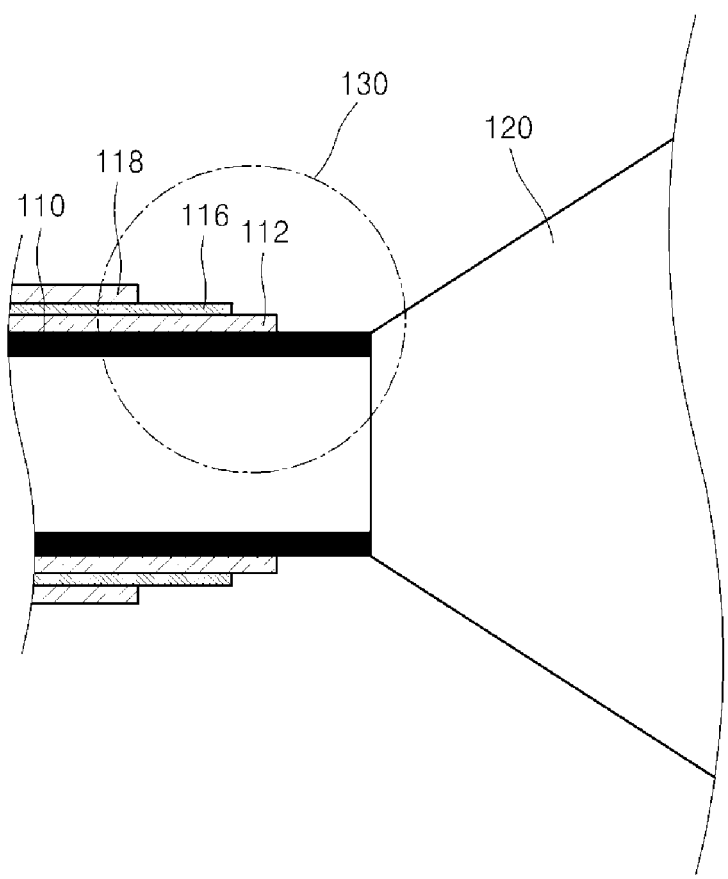
FIG. 3 is a partial section view of an exposed portion of a syringe capable of measuring an inner temperature of a patient body in accordance with another embodiment of the present invention.

FIG. 3 is a partial section view obtained by enlarging one end of a syringe needle connected to a body 120 in a syringe capable of measuring an inner temperature of a patient body according to another embodiment of the present invention.

In this embodiment, the syringe needle 110 is connected at one end of thereof to the body 120 and is formed at the end thereof with an exposed portion 130 at which a surface of a metallic syringe needle 110 and a dissimilar metal layer 116 are exposed.

The exposed portion 130 may be formed by coating an insulation layer or depositing a dissimilar metal layer such that a certain area is not coated or deposited through a mask, and the surface of the metallic syringe needle 110 and the dissimilar metal layer 116 exposed to the outside serve as a connecting portion wire-connected to a voltage measuring unit.

Figure 4:
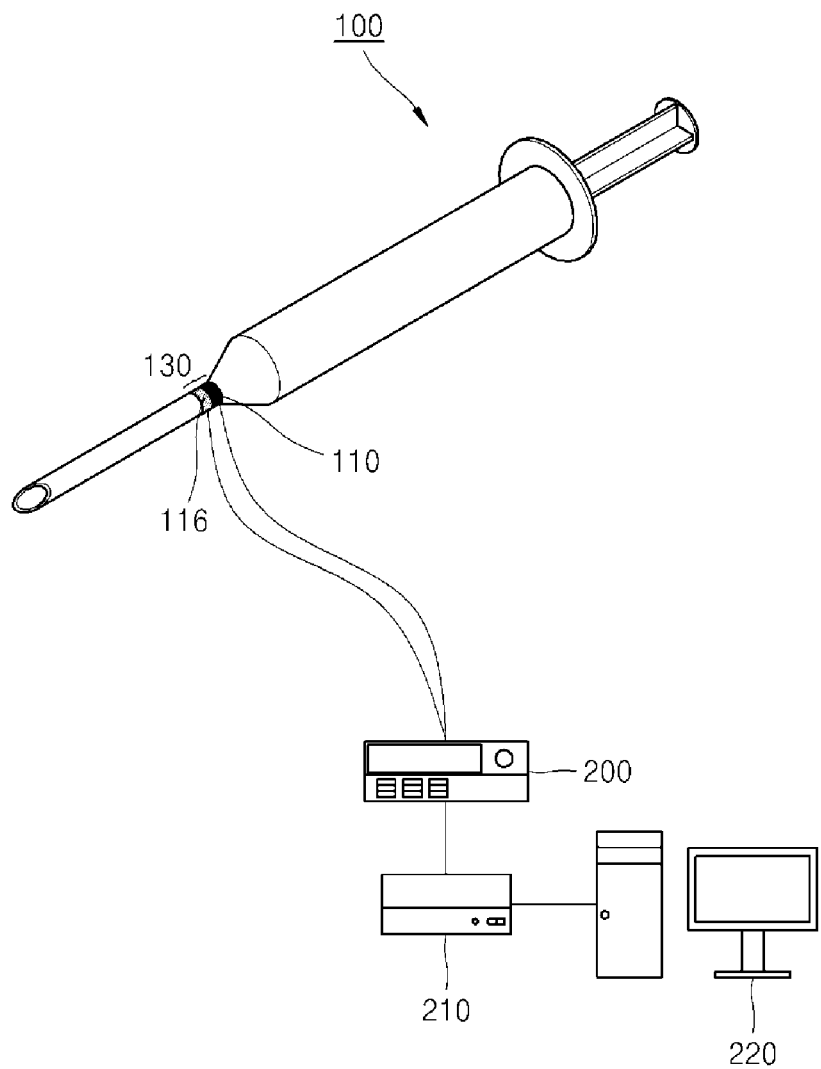
FIG. 4 is a diagram showing a state in which a voltage measuring unit, a data collection/analysis unit, and a temperature display unit are connected to the syringe.

FIG. 4 shows a syringe capable of measuring an inner temperature of a patient body according to a further embodiment of the invention, which further includes a voltage measuring unit 220 wire-connected to the exposed portion 130 to measure thermo-electromotive force, and a data collection/analysis unit 210 for measuring an inner temperature of a patient body through analysis of the measured voltage information. The syringe may further include a temperature display unit 220 which displays temperature information.

In some embodiments, however, the voltage measuring unit may be located inside the syringe to measure thermo-electromotive force, instead of being connected to the exposed portion, and the temperature display unit may be attached to the body of the syringe or be remotely connected to the body thereof using a wireless data transmission module to display the measured temperature.

FIG. 5 shows a portable syringe 100 which includes a temperature display unit 220 capable of displaying an inner temperature of a patient body in a body of the syringe 100.

As shown in FIG. 6, an inner temperature of a region causing pain in a patient body can be identified by the temperature display unit 220 remotely connected to the body of the syringe 100 by a wireless data transmission module 230.

Method of Manufacturing Syringe Capable of Measuring Inner Temperature

Hereinafter, a method of manufacturing the syringe 100 capable of measuring an inner temperature of a patient body according to one embodiment of the invention will be described in detail.

FIGS. 7a to 7d are diagrams of a method of manufacturing a syringe capable of measuring an inner temperature of a patient body in accordance with one embodiment of the present invention.

Figure 7A:
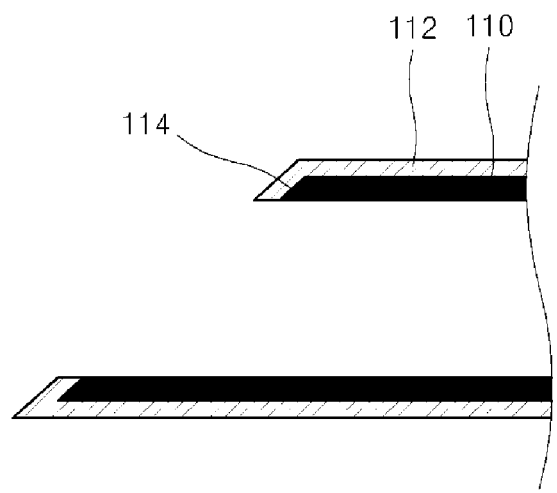
FIGS. 7a to 7d are diagrams of a method of manufacturing a syringe capable of measuring an inner temperature of a patient body in accordance with one embodiment of the present invention.

First, referring to FIG. 7a, a first insulation layer 112 is formed by coating an insulating material on a surface 100 of a metallic syringe needle 110. The insulating material is deposited on the surface of the syringe needle 110 through vapor deposition or the like to form the first insulation layer. Here, an inclined surface 114 of a tip portion of the syringe needle is also deposited.

Figure 7B:
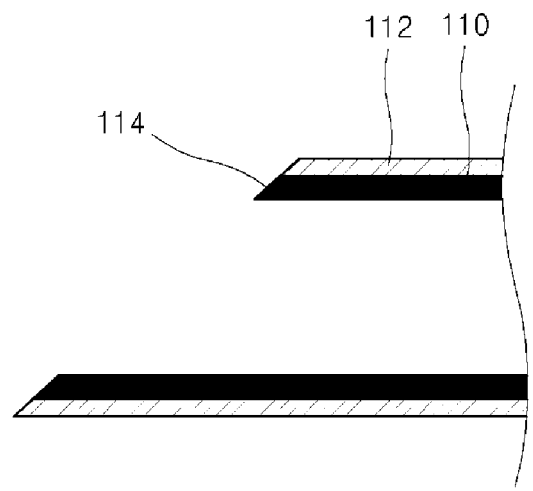

Next, referring to FIG. 7b, the inclined surface 114 of the tip portion of the syringe needle 110 is exposed. This process may be performed by mechanically polishing or wet etching the inclined surface 114 of the tip portion of the syringe needle coated with the first insulation layer.

Figure 7C:
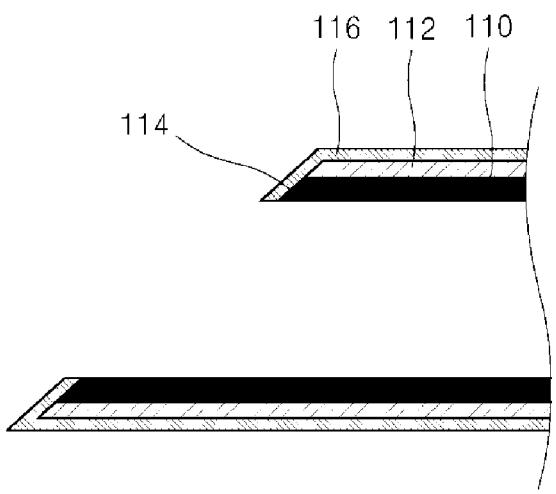
Figure 7D:
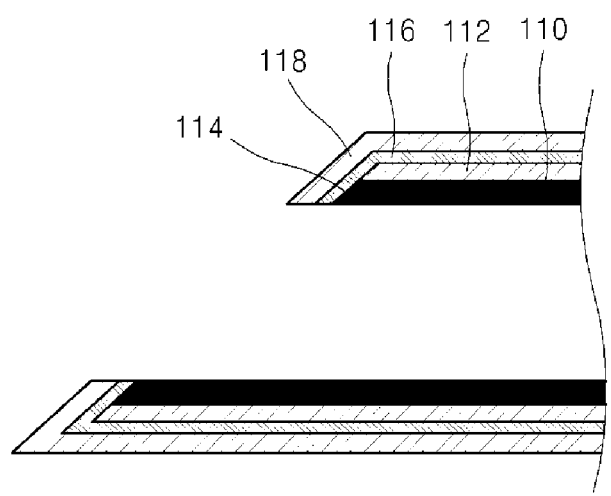

Next, referring to FIG. 7c, a dissimilar metal layer 116 formed of a different metal from that of the syringe needle is deposited on the first insulation layer 112 to contact an exposed portion of the metallic syringe needle 110. That is, the metallic syringe needle 110 and the dissimilar metal layer 116 contact each other on the exposed portion of the inclined surface 114 of the tip portion of the syringe, which is formed by mechanical polishing or wet etching, to form a thermocouple junction therebetween.

Here, the dissimilar metal layer 116 may be deposited through metal sputtering, which is a vacuum deposition process in which ionized gas of plasma is accelerated to collide with a target and to emit atoms, thereby forming a film on a substrate. However, it should be understood that the present invention is not limited thereto. Advantageously, the dissimilar metal layer 116 has a thickness of 0.01 μm to 10 μm to act as a thermocouple based on a thermocouple phenomenon. Preferably, the dissimilar metal layer 116 has a thickness of 0.1 μm to 10 μm.

Finally, an insulating material is coated on the dissimilar metal layer 116 to form a second insulation layer 118. The second insulation layer 118 is coated on the dissimilar metal layer 116 through vapor deposition to reduce influence of external noise.

Through the aforementioned process, a syringe capable of measuring an inner temperature of a patient body, in which a thermocouple junction is formed at a tip portion of a syringe needle, can be manufactured.

As shown in FIG. 3, an exposed portion 130 at which a surface of the metallic syringe needle and a similar metal layer are exposed outside may be formed through a masking process during coating of the insulating material. The exposed portion 130 may be formed at one end of the syringe needle through which the syringe needle is connected to the body.

Referring to FIG. 4, a voltage measuring unit 200 may be wire-connected to the exposed surface of the syringe needle 110 and the dissimilar metal layer 116. That is, the voltage measuring unit 200 for measuring a thermo-electromotive force is wire-connected to the exposed portion 130, and a data collection/analysis unit 210 analyzes the measured voltage information to calculate an inner temperature of a patient body. Here, the voltage measuring unit may be wire-connected thereto through an electrode material, such as silver paste or copper paste.

Alternatively, as shown in FIGS. 5 and 6, the voltage measuring unit for measuring a thermo-electromotive force may be located in the syringe, and the temperature display unit may be attached to the body or remotely connected thereto using a wireless data transmission module 230, instead of being formed on the exposure unit 130.

Now, the present invention will be described in more detail with reference to one example.

Example

Manufacture of Syringe Capable of Measuring Inner Temperature

Parylene was coated to a thickness of 1.5 μm on a surface of a syringe needle formed of iron and having a diameter of 16 gauge (1.6 mm) through vapor deposition. Then, an inclined surface of a tip portion of a syringe needle was mechanically polished, and constantan was deposited to a thickness of 0.2 μm on the parylene coating through metal sputtering. Parylene was further coated on the deposited constantan layer to a thickness of 1.0 μm to form a syringe having a syringe needle as shown in FIGS. 1 and 2.

Next, thermo-electromotive force between constantan and iron was measured while changing the temperature of the tip portion of the syringe needle using a voltage measuring unit. Results are shown in FIG. 8.

Figure 8:
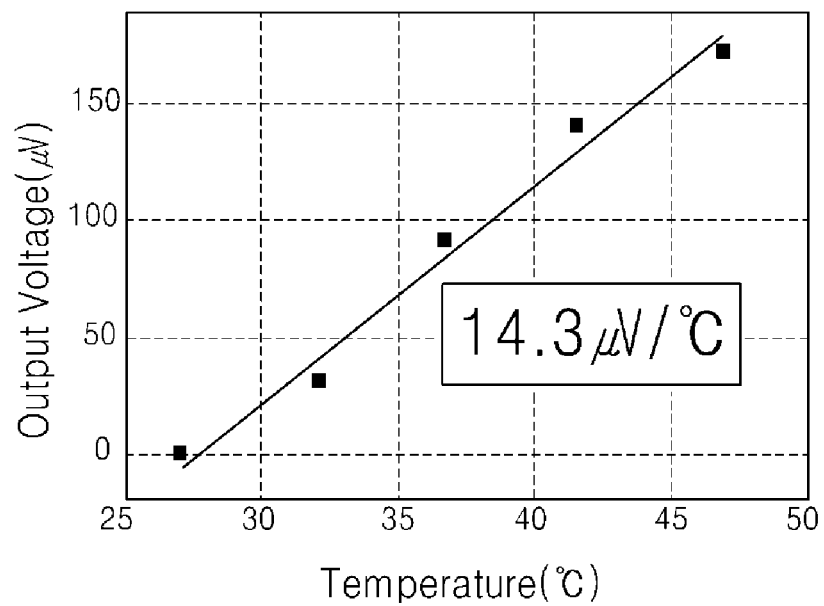
FIG. 8 is a graph depicting sensitivities identified by measuring thermo-electromotive force according to temperature change at a tip portion of the syringe in accordance with the embodiment of the present invention.

From FIG. 8, it can be seen that thermo-electromotive force increased with increasing temperature of the tip end and had a rate of about 14.3 μV/° C.

Thus, it can be seen that when a medicine is administered into a patient body through the syringe needle, the inner temperature of the human body can be measured due to the thermocouple junction formed at the tip portion of the syringe needle.

As described above, the syringe capable of measuring an inner temperature of a patient body according to the invention may directly measure a temperature of a region causing pain of a patient body with a thermo-electromotive force generated from a thermocouple junction formed on an inclined surface of a tip portion of the syringe needle, whereby the region causing pain can be diagnosed while allowing administration of medicine thereto, thereby enabling efficient treatment and significantly reducing potential harm due to drug abuse.

Although some exemplary embodiments have been described herein, it should be understood by those skilled in the art that these embodiments are given by way of illustration only, and that various modifications, variations and alterations can be made without departing from the spirit and scope of the invention. The scope of the present invention should be defined by the appended claims and equivalents thereof.

What is claimed is:

1. A syringe capable of measuring an inner temperature of a patient body, comprising:
   a first insulation layer formed by coating a first insulating material on a surface of a metallic syringe needle;
   a dissimilar metal layer formed by depositing a different metal from that of the syringe needle on an inclined surface of a tip portion of the syringe needle to contact the inclined surface of the tip portion of the syringe needle; and
   a second insulation layer formed by coating a second insulating material on the dissimilar metal layer.

2. The syringe according to claim 1, further comprising:
   an exposed portion at which a surface of the metallic syringe needle and the dissimilar metal layer are exposed to an outside.

3. The syringe according to claim 2, further comprising:
   a voltage measuring unit wire-connected to the exposed portion to measure thermo-electromotive force; and a data collection/analysis unit for analyzing measured voltage information and calculating an inner temperature of a patient body.

4. The syringe according to claim 1, wherein at least one of the first and second insulating materials is a material allowing vapor deposition.

5. The syringe according to claim 4, wherein at least one of the first and second insulating materials is parylene, polyimide, or epoxy resins.

6. The syringe according to claim 1, wherein the syringe needle is formed of iron or copper.

7. The syringe according to claim 1, wherein the dissimilar metal layer is formed of constantan, gold, or nickel.

8. The syringe according to claim 1, wherein the dissimilar metal layer has a thickness of 0.01 μm to 10 μm.

9. The syringe according to claim 1, further comprising:
a voltage measuring unit located within the syringe to measure thermo-electromotive force; and
a temperature display unit attached to a body of the syringe or remotely connected to the body of the syringe using a wireless data transmission module.

10. A method of manufacturing a syringe for measuring an inner temperature of a patient body, the method comprising:
1) coating a first insulating material on a surface of a metallic syringe needle;
2) exposing the metallic syringe needle to an outside on an inclined surface of a tip portion of the syringe needle;
3) depositing a dissimilar metal layer formed of a different metal from that of the syringe needle on the insulation material such that the dissimilar metal layer contacts the metallic syringe needle exposed to the outside; and
4) coating a second insulating material on the dissimilar metal layer to obtain the syringe which comprises:
a first insulation layer formed by coating the first insulating material on the surface of the metallic syringe needle;
the dissimilar metal layer formed by depositing the different metal from that of the syringe needle on the inclined surface of the tip portion of the syringe needle to contact the inclined surface of the tip portion of the syringe needle; and
a second insulation layer formed by coating the second insulating material on the dissimilar metal layer.

11. The method according to claim 10, wherein, in at least one of 1) and 4), coating at least one of first and second insulating material s, an exposed portion at which the surface of the metallic syringe needle and the dissimilar metal layer are exposed to the outside is formed through a masking process.

12. The method according to claim 11, further comprising: providing a voltage measuring unit wire-connected to the exposed portion to measure thermo-electromotive force, and a data collection/analysis unit for analyzing measured voltage information and calculating an inner temperature of a patient body.

13. The method according to claim 10, wherein, in 2) exposing the metallic syringe needle, the metallic syringe needle is exposed to the outside on the inclined surface of the tip portion of the syringe needle through mechanical polishing or wet etching.

14. The method according to claim 10, wherein, in at least one of 1) and 4), coating at least one of first and second insulating materials, the at least one of the first and second insulating materials is coated through vapor deposition.

15. The method according to claim 10, wherein, in 3) depositing a dissimilar metal layer, the dissimilar metal layer is deposited through metal sputtering.

16. The method according to claim 10, wherein the dissimilar metal layer is deposited to a thickness of 0.01 μm to 10 μm.

17. The method according to claim 10, further comprising: providing a voltage measuring unit located within the syringe to measure thermo-electromotive force, and a temperature display unit attached to a body of the syringe or remotely connected to the body of the syringe using a wireless data transmission module.

* * * * *